(12) United States Patent
Wickham et al.

(10) Patent No.: US 6,576,456 B2
(45) Date of Patent: *Jun. 10, 2003

(54) CHIMERIC ADENOVIRUS FIBER PROTEIN

(75) Inventors: Thomas J. Wickham, Bethesda, MD (US); Erik Falck-Pedersen, Dobbs Ferry, NY (US); Petrus W. Roelvink, Gaithersburg; Joseph T. Bruder, New Market, both of MD (US); Jason Gall, New York, NY (US); Imre Kovesdi, Rockville, MD (US)

(73) Assignees: Cornell Research Foundation, Inc., Ithaca, NY (US); GenVec, Inc., Gaithersburg, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 167 days.

This patent is subject to a terminal disclaimer.

(21) Appl. No.: 09/326,447

(22) Filed: Jun. 4, 1999

(65) Prior Publication Data

US 2002/0099024 A1 Jul. 25, 2002

Related U.S. Application Data

(63) Continuation of application No. 08/906,758, filed on Aug. 5, 1997, which is a continuation of application No. 08/395,381, filed on Feb. 21, 1995, now Pat. No. 5,770,442.

(51) Int. Cl.[7] .......................... C12N 7/01; C12N 15/861; A61K 38/12; C07K 14/00; C07H 21/04

(52) U.S. Cl. .................... 435/235.1; 530/324; 530/350; 435/320.1; 536/23.1; 536/23.4; 536/23.72

(58) Field of Search .................................. 530/324, 350; 435/320.1, 235.1; 536/23.1, 23.4, 23.72

(56) References Cited

U.S. PATENT DOCUMENTS

| | | | |
|---|---|---|---|
| 4,487,829 A | 12/1984 | Sharp et al. ................... 435/5 |
| 4,517,686 A | 5/1985 | Ruoslahti et al. .............. 623/1 |
| 4,578,079 A | 3/1986 | Ruoslahti et al. ............. 623/11 |
| 4,593,002 A | 6/1986 | Dulbecco .................. 435/91.41 |
| 4,792,525 A | 12/1988 | Ruoslahti et al. ........... 435/402 |
| 5,166,320 A | 11/1992 | Wu et al. .................... 530/395 |
| 5,204,445 A | 4/1993 | Plow et al. ................. 530/326 |
| 5,223,394 A | 6/1993 | Wallner .......................... 435/6 |
| 5,223,409 A | 6/1993 | Ladner et al. .............. 435/69.7 |
| 5,332,567 A | 7/1994 | Goldenberg et al. ....... 424/1.49 |
| 5,349,053 A | 9/1994 | Landolfi ..................... 530/351 |
| 5,403,484 A | 4/1995 | Ladner et al. ............ 435/235.1 |
| 5,443,953 A | 8/1995 | Hansen et al. ............. 424/1.49 |
| 5,521,291 A | 5/1996 | Curiel et al. ............. 530/391.7 |

(List continued on next page.)

FOREIGN PATENT DOCUMENTS

| | | |
|---|---|---|
| WO | WO 88/04692 | 6/1988 |
| WO | WO 88/05077 | 7/1988 |
| WO | WO 90/12087 | 10/1990 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/06180 | 4/1992 |
| WO | WO 92/13081 | 8/1992 |
| WO | WO 93/07282 | 4/1993 |
| WO | WO 93/07283 | 4/1993 |
| WO | WO 93/25234 | 12/1993 |
| WO | WO 94/06920 | 3/1994 |
| WO | WO 94/10323 | 5/1994 |
| WO | WO 94/15644 | 7/1994 |
| WO | WO 94/17832 | 8/1994 |
| WO | WO 94/24299 | 10/1994 |
| WO | WO 95/05201 | 2/1995 |
| WO | WO 95/26412 | 10/1995 |
| WO | WO 95/31187 | 11/1995 |
| WO | WO 95/31566 | 11/1995 |
| WO | WO 96/07734 | 3/1996 |
| WO | WO 97/24453 | 7/1997 |
| WO | WO 97/38723 | 10/1997 |
| WO | WO 98/07865 | 2/1998 |
| WO | WO 98/11221 | 3/1998 |
| WO | WO 98/13499 | 4/1998 |
| WO | WO 98/22609 | 5/1998 |
| WO | WO 98/32842 | 7/1998 |
| WO | WO 98/40509 | 9/1998 |

OTHER PUBLICATIONS

Athapilly et al., *J. Mol. Biol.*, 242, 430–455 (1994).
Kinloch et al., *J. Biol. Chem.*, 259, 6431–6436 (1984).
Roberts et al., *Science*, 232, 1148–1151 (1986).
Stewart et al., *EMBO J.*, 12, 2589–2599 (1993).
Toogood et al., *J. Gen. Virol.*, 73, 1429–1435 (1992).
Xia et al., *Structure*, 2, 1259–1270 (1994).
Albiges–Rizo et al., *J. Biol. Chem.*, 266 (6), 3961–3967 (1991).
Bai et al., *J. Virol.*, 67 (9), 5198–5205 (1993).
Ball–Goodrich et al., *Virology*, 184, 175–186 (1991).
Batra et al., *Gene Therapy*, 1, 255–260 (1994).
Boursnell et al., *Gene*, 13, 311–317 (1981).
Caillet–Boudin et al., *J. Mol. Biol.*, 217, 477–486 (1991).
Chroboczek et al., *Virology*, 186, 280–285 (1992).
Chu et al., *Gene Therapy*, 1, 292–299 (1994).
Cotten et al., *Proc. Natl. Acad. Sci. USA*, 89, 6094–6098 (1992).
Cotten et al., *Proc. Natl. Acad. Sci.*, 87, 4033–4037 (1990).
Crawford–Miksza et al., *J. Virol.*, 70 (3), 1836–1844 (1996).
Crompton et al., *J. Gen. Virol.*, 75 (1), 133–139 (1994).

(List continued on next page.)

*Primary Examiner*—David Guzo
*Assistant Examiner*—Gerald G. Leffers, Jr.
(74) *Attorney, Agent, or Firm*—Leydig, Voit & Mayer, Ltd.

(57) ABSTRACT

The invention provides a chimeric adenovirus fiber protein including a nonnative amino acid sequence, and a chimeric adenovirus fiber protein lacking a native amino acid receptor-binding sequence. The chimeric protein trimerizes when produced in a mammalian cell.

21 Claims, 15 Drawing Sheets

U.S. PATENT DOCUMENTS

| | | | |
|---|---|---|---|
| 5,543,328 A | 8/1996 | McClelland et al. | 435/320.1 |
| 5,547,932 A | 8/1996 | Curiel et al. | 435/85 |
| 5,559,099 A | 9/1996 | Wickham et al. | 514/44 |
| 5,571,698 A | 11/1996 | Ladner et al. | 435/69.7 |
| 5,622,699 A | 4/1997 | Ruoslahti et al. | 424/93.6 |
| 5,661,133 A | 8/1997 | Leiden et al. | 514/44 |
| 5,672,344 A | 9/1997 | Kelley et al. | 424/93.2 |
| 5,674,722 A | 10/1997 | Mulligan et al. | 435/456 |
| 5,693,509 A | 12/1997 | Cotten et al. | 435/456 |
| 5,695,991 A | 12/1997 | Lindholm et al. | 435/320.1 |
| 5,712,136 A | 1/1998 | Wickham et al. | 435/456 |
| 5,731,190 A | 3/1998 | Wickham et al. | 435/320.1 |
| 5,756,086 A | 5/1998 | McClelland et al. | 424/93.2 |
| 5,770,442 A | 6/1998 | Wickham et al. | 435/370.1 |
| 5,885,808 A | 3/1999 | Spooner et al. | 435/456 |

OTHER PUBLICATIONS

Curiel et al., *Proc. Natl. Acad. Sci. USA*, 88, 8850–8854 (1991).
Defer et al., *J. Virol*, 64 (8), 3661–3673 (1990).
Derwent Publications Ltd., Derwent WPI, Week 9017, AN 90–129060/17 (JP 2,078,631 abstract).
Etienne–Julan et al., *J. Gen. Virol.*, 73, 3251–3255 (1992).
Falck–Pedersen, "Gene Therapy for Cystic Fibrosis", Abstract of Grant Application No. 1 P01 HL51746–01UB: 0004, submitted to the National Institutes of Health, (1994).
Falgout et al., *J. Virol.*, 62 (2), 622–625 (1988).
Green et al., *EMBO Journal*, 2 (8), 1357–1365 (1983).
Grubb et al., *Nature*, 371, 802–806 (1994).
Han et al., *Proc. Natl. Acad. Sci. USA*, 92, 9747–9751 (1995).
Henry et al., *J. Virol.*, 68 (8), 5239–5246 (1994).
Hong et al., *Virology*, 185 (2), 758–767 (1991).
Horvath et al., *J. Virol.*, 62 (1), 341–345 (1988).
Huang et al., *J. Virol.*, 69 (4), 2257–2263 (1995).
Karayan et al., *Virology*, 202, 782–785 (1994).
Komoriya et al., *J. Biol. Chem.*, 266 (23), 15075–15079 (1991).
Mastrangeli et al., *Ped. Pulm., Suppl. 12*, 230, Abstr. No. 180 (1995).
Mastrangeli et al., *Human Gene Therapy*, 7, 79–87 (1996).
Mathias et al., *J. Virol.*, 68 (10), 6811–6814 (1994).
Michael et al., *Gene Therapy*, 2, 660–668 (1995).
Michael et al., *J. Biol. Chem.*, 268, 6866–6869 (1993).
Michael et al., presented at Adenovirus Workshop: St. Andrews University, p. 52 (Jul. 13–15, 1995).
Miller et al., *FASEB J.*, 9, 190–199 (1995).
Neda et al., *J. Biol. Chem.*, 266 (22), 14143–14146 (1991).
Nemerow et al., in *Biology of Vitronectins and Their Receptors*(Preissner et al., eds), 177–184 (Elsevier Science Publishers, 1993).
Nemerow et al., *Trends In Cell Biology*, 4, 52–55 (1994).
Novelli et al., *Virology*, 185, 365–376 (1991).
Peteranderl et al., *Biochemistry*, 31, 12272–12276 (1992).
Russell et al., *Nucleic Acids Research*, 21 (5), 1081–1085 (1993).
Signas et al., *J. Virol.*, 53 (2), 672–678 (1985).
Wagner et al., *Proc. Natl. Acad. Sci. USA*, 89, 6099–6103 (1992).
Watkins et al., presented at Keystone Symposium on Molecular and Cellular Biology, Abst. No. 336 (Taos: NM, Feb. 22–28, 1996).
Wickham et al., *Cell*, 73, 309–319 (1993).
Wickham et al., *Gene Therapy*, 2, 750–756 (1995).
Wickham et al., *J. Cell Biol.*, 127, 257–264 (1994).
Bergelson et al., *Science*, 275, 1320–1323 (1997).
Douglas et al., *Nature Biotechnology*, 14 1574–1578 (1996).
Gilmore et al., *EMBO Journal*, 15 (11), 2651–2658 (1996).
Kleiboeker, *Virus Research*, 39, 299–309 (1995).
Stevenson et al., *J. Virol.*, 69 (5), 2850–2857 (1995).

Knob: (Ad5) amino acids 405-592

Shaft: (Ad5) amino acids 1-404

Penton Base

Fiber start                                                NdeI
ATGAAGCGCGCAAGACCGTCTGAAGATACCTTCAACCCCGTGTATCCATATGAC
▶MetLysArgAlaArgProSerGluAspThrPheAsnProValTyrProTyrAsp (SEQ ID NO:9)

p193 Ad5 NdeI/SalI
(7.29 kB)

MunI
GCCCAAGAATAAAGAATCGTTTGTGTTATGTTTCAACGTGTTTATTTTT<u>CAATTG</u>
▶AlaGlnGlu•••

(SEQ ID NO: 11)

p193 FC (F-)
(5.604 kB)

NdeI    BamHI                                                              MunI
CATATGGAGGATCCAATAAAGAATCGTTTGTGTTATGTTTCAACGTGTTTATTTTTCAATTG (SEQ ID NO: 13)

p193 FC (HSF; RGD)
(7.14 kB)

SpeI                                                 ScaI
GGAGGTGGAGGTGGAACTAGTTTTGGACGCGGAGACATTCGCAATTAAAGTACTGGATTCATGACT
▶GlyGlyGlyGlyGlyThrSerPheGlyArgGlyAspIleArgAsn•••

BamHI
CTAGACTTAATTAAGGATCC (SEQ ID NO: 14)

pGBS.59-100 (HSF;RGD)
(17.106 kB)

SpeI
GAACTCGGAGGTGGAGGTGGAACTAGTTTTGGACGCGGAGACATTCGCAATTAA
▶GluLeuGlyGlyGlyGlyGlyThrSerPheGlyArgGlyAspIleArgAsn•••
ScaI                                        BamHI
AGTACTGGATTCATGACTCTAGACTTAATTAAGGATCCAATAAA (SEQ ID NO: 17)

pAcSG2 (HSF;RGD)
(7095 bp)

```
          SpeI                                    ScaI
GGAGGTGGAGGTGGAACTAGTTTTGGACGCGGAGACATTCGCAATTAAAGTACTGGATTCATGACT
▶ GlyGlyGlyGlyGlyThrSerPheGlyArgGlyAspIleArgAsn•••

BamHI
CTAGACTTAATTAAGGATCC
```

(SEQ ID NO: 14)

```
SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
          (A) LENGTH: 31 base pairs
          (B) TYPE: nucleic acid
          (C) STRANDEDNESS: single
          (D) TOPOLOGY: unknown (ii) MOLECULE TYPE: DNA (synthetic)

(xi) SEQUENCE DESCRIPTION: SEQ ID NO:1:

GCCGCTCGAG TTGCAGATGA AACGCGCCAG A                                31
```

(2) INFORMATION FOR SEQ ID NO:2:

(i) SEQUENCE CHARACTERISTICS:
        (A) LENGTH: 35 base pairs
        (B) TYPE: nucleic acid
        (C) STRANDEDNESS: single
        (D) TOPOLOGY: unknown (ii) MOLECULE TYPE: DNA (synthetic)

(xi) SEQUENCE DESCRIPTION: SEQ ID NO:2:

AGGGCCCGGG AGGATCCTTA TTCTTGGGCA ATGTA                        35

(2) INFORMATION FOR SEQ ID NO:3:

(i) SEQUENCE CHARACTERISTICS:
        (A) LENGTH: 55 base pairs
        (B) TYPE: nucleic acid
        (C) STRANDEDNESS: single
        (D) TOPOLOGY: unknown (ii) MOLECULE TYPE: DNA (synthetic)

(xi) SEQUENCE DESCRIPTION: SEQ ID NO:3:

TATGGAGGAT CCAATAAAGA ATCGTTTGTG TTATGTTTCA ACGTGTTTAT TTTTC      55

(2) INFORMATION FOR SEQ ID NO:4:

(i) SEQUENCE CHARACTERISTICS:
        (A) LENGTH: 57 base pairs
        (B) TYPE: nucleic acid
        (C) STRANDEDNESS: single
        (D) TOPOLOGY: unknown (ii) MOLECULE TYPE: DNA (synthetic)

(xi) SEQUENCE DESCRIPTION: SEQ ID NO:4:

AATTGAAAAA TAAACACGTT GAAACATAAC ACAAACGATT CTTTATTGGA TCCTCCA    57

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: unknown (ii) MOLECULE TYPE: DNA (synthetic)

(xi) SEQUENCE DESCRIPTION: SEQ ID NO:5:

AACCCGGTGT ACCCATATGA TGAAAGCAGC TC                           32

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: unknown (ii) MOLECULE TYPE: DNA (synthetic)

(xi) SEQUENCE DESCRIPTION: SEQ ID NO:6:

AATGGATCCT CAGTCATCTT CTCTAATATA GGAAA                        35

(2) INFORMATION FOR SEQ ID NO:7:

(i) SEQUENCE CHARACTERISTICS:
        (A) LENGTH: 79 base pairs (B) TYPE: nucleic acid
    (C) STRANDEDNESS: single
    (D) TOPOLOGY: unknown (ii) MOLECULE TYPE: DNA (synthetic)

(xi) SEQUENCE DESCRIPTION: SEQ ID NO:7:

ATGGATCCAG TACTTTAATT GCGAATGTCT CCGCGTCCAA AACTAGTTCC ACCTCCACCT        60

CCGAGTTCAT GGATCAAAT                                                    79

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Val Pro Arg Gly Ser
1               5

(2) INFORMATION FOR SEQ ID NO:9:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..54

(xi) SEQUENCE DESCRIPTION: SEQ ID NO:9:

ATG AAG CGC GCA AGA CCG TCT GAA GAT ACC TTC AAC CCC GTG TAT CCA         48
Met Lys Arg Ala Arg Pro Ser Glu Asp Thr Phe Asn Pro Val Tyr Pro
 1               5                  10                  15

TAT GAC                                                                 54
Tyr Asp (2) INFORMATION FOR SEQ ID NO:10:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:10:

Met Lys Arg Ala Arg Pro Ser Glu Asp Thr Phe Asn Pro Val Tyr Pro
 1               5                  10                  15

Tyr Asp (2) INFORMATION FOR SEQ ID NO:11:

(i) SEQUENCE CHARACTERISTICS:
        (A) LENGTH: 55 base pairs
        (B) TYPE: nucleic acid
        (C) STRANDEDNESS: double
        (D) TOPOLOGY: linear (ii) MOLECULE TYPE: DNA (genomic)

(ix) FEATURE:
            (A) NAME/KEY: CDS
            (B) LOCATION: 1..9

(xi) SEQUENCE DESCRIPTION: SEQ ID NO:11:

GCC CAA GAA TAAAGAATCG TTTGTGTTAT GTTTCAACGT GTTTATTTTT CAATTG         55
Ala Gln Glu
  1

(2) INFORMATION FOR SEQ ID NO:12:

(i) SEQUENCE CHARACTERISTICS:
            (A) LENGTH: 3 amino acids
            (B) TYPE: amino acid
            (D) TOPOLOGY: linear (ii) MOLECULE TYPE: protein (xi) SEQUENCE DESCRIPTION: SEQ ID NO:12:

Ala Gln Glu
  1

(2) INFORMATION FOR SEQ ID NO:13:

(i) SEQUENCE CHARACTERISTICS:
            (A) LENGTH: 62 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:13:

CATATGGAGG ATCCAATAAA GAATCGTTTG TGTTATGTTT CAACGTGTTT ATTTTTCAAT       60

TG                                                                    62

(2) INFORMATION FOR SEQ ID NO:14:

(i) SEQUENCE CHARACTERISTICS:
            (A) LENGTH: 86 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..45

(xi) SEQUENCE DESCRIPTION: SEQ ID NO:14:

GGA GGT GGA GGT GGA ACT AGT TTT GGA CGC GGA GAC ATT CGC AAT            45
Gly Gly Gly Gly Gly Thr Ser Phe Gly Arg Gly Asp Ile Arg Asn
  1               5                  10                  15

TAAAGTACTG GATTCATGAC TCTAGACTTA ATTAAGGATC C                          86

(2) INFORMATION FOR SEQ ID NO:15:

(i) SEQUENCE CHARACTERISTICS:
            (A) LENGTH: 15 amino acids
            (B) TYPE: amino acid
            (D) TOPOLOGY: linear (ii) MOLECULE TYPE: protein (xi) SEQUENCE DESCRIPTION: SEQ ID NO:15:

Gly Gly Gly Gly Gly Thr Ser Phe Gly Arg Gly Asp Ile Arg Asn (2) INFORMATION FOR SEQ ID NO:16:

(i) SEQUENCE CHARACTERISTICS:
        (A) LENGTH: 98 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..51

(xi) SEQUENCE DESCRIPTION: SEQ ID NO:16:

```
GAA CTC GGA GGT GGA GGT GGA ACT AGT TTT GGA CGC GGA GAC ATT CGC      48
Glu Leu Gly Gly Gly Gly Gly Thr Ser Phe Gly Arg Gly Asp Ile Arg
 1               5                  10                  15

AAT TAAAGTACTG GATTCATGAC TCTAGACTTA ATTAAGGATC CAATAAA              98
Asn
```

(2) INFORMATION FOR SEQ ID NO:17:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:17:

```
Glu Leu Gly Gly Gly Gly Gly Thr Ser Phe Gly Arg Gly Asp Ile Arg
 1               5                  10                  15

Asn
```

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..45

(xi) SEQUENCE DESCRIPTION: SEQ ID NO:18:

```
GGA GGT GGA GGT GGA ACT AGT TTT GGA CGC GGA GAC ATT CGC AAT          45
Gly Gly Gly Gly Gly Thr Ser Phe Gly Arg Gly Asp Ile Arg Asn
 1               5                  10                  15
```

CHIMERIC ADENOVIRUS FIBER PROTEIN

CROSS REFERENCE TO RELATED APPLICATIONS

This is a continuation application of copending U.S. Patent Application Ser. No. 08/906,758 filed Aug. 5, 1997, which is a continuation application of U.S. Pat. Application Ser. No. 08/395,381, filed Feb. 21,1995, now U.S. Pat. No. 5,770,442.

This invention was made in part with United States Government support under Grant Number HL51746-01 awarded by the National Institutes of Health. The United States Government may have certain rights in this invention.

TECHNICAL FIELD OF THE INVENTION

The present invention relates to a recombinant adenovirus comprising a chimeric adenoviral fiber protein and the use of a recombinant adenovirus comprising a chimeric adenoviral fiber protein in gene therapy.

BACKGROUND OF THE INVENTION

Adenoviruses belong to the family Adenoviridae, which is divided into two genera, namely *Mastadenovirus* and *Aviadenovirus*. Adenoviruses are nonenveloped, regular icosahedrons 65–80 nm in diameter (Home et al., *J. Mol. Biol.,* 1, 84–86 (1959)). The capsid is composed of 252 capsomeres of which 240 are hexons and 12 are pentons (Ginsberg et al., *Virology,* 28, 782–783 (1966)). The hexons and pentons are derived from three different viral polypeptides (Maizel et al., *Virology,* 36, 115–125 (1968); Weber et al, *Virology,* 76, 709–724 (1977)). The hexon comprises three identical polypeptides of 967 amino acids each, namely polypeptide II (Roberts et al., *Science,* 232, 1148–1151 (1986)). The penton contains a penton base, which is bound to the capsid, and a fiber, which is noncovalently bound to and projects from the penton base. The fiber protein comprises three identical polypeptides of 582 amino acids each, namely polypeptide IV. The adenovirus serotype 2 (Ad2) penton base protein is an 8×9 nm ring-shaped complex composed of five identical protein subunits of 571 amino acids each, namely polypeptide III (Boudin et al., *Virology,* 92, 125–138 (1979)). Proteins IX, VI, and IIIa are also present in the adenoviral coat and are thought to stabilize the viral capsid (Stewart et al., *Cell,* 67, 145–154 (1991); Stewart et al., *EMBO J.,* 12(7), 2589–2599 (1993)).

Once an adenovirus attaches to a cell, it undergoes receptor-mediated internalization into clathrin-coated endocytic vesicles of the cell (Svensson et al., J. Virol., 51, 687–694 (1984); Chardonnet et al., *Virology,* 40, 462–477 (1970)). Virions entering the cell undergo a stepwise disassembly in which many of the viral structural proteins are shed (Greber et al, *Cell,* 75, 477–486 (1993)). During the uncoating process, the viral particles cause disruption of the cell endosome by a pH-dependent mechanism (Fitzgerald et al., *Cell,* 32, 607–617 (1983)), which is still poorly understood. The viral particles are then transported to the nuclear pore complex of the cell (Dales et al., *Virology,* 56, 465–483 (1973)), where the viral genome enters the nucleus, thus initiating infection.

An adenovirus uses two separate cellular receptors, both of which must be present, to efficiently attach to and infect a cell (Wickham et al., *Cell,* 73, 309–319 (1993)). First, the Ad2 fiber protein attaches the virus to a cell by binding to an, as yet, unidentified receptor. Then, the penton base binds to $\alpha_v$ integrins, which are a family of a heterodimeric cell-surface receptors that mediate cellular adhesion to the extracellular matrix molecules fibronectin, vitronectin, laminin, and collagen, as well as other molecules (Hynes, *Cell,* 69, 11–25 (1992)), and play important roles in cell signaling processes, including calcium mobilization, protein phosphorylation, and cytoskeletal interactions (Hynes, supra).

The fiber protein is a trimer (Devaux et al.,*J. Molec. Biol.,* 215, 567–588 (1990)) consisting of a tail, a shaft, and a knob. The fiber shaft region is composed of repeating 15 amino acid motifs, which are believed to form two alternating b-strands and b-bends (Green et al., EMBO J., 2, 1357–1365 (1983)). The overall length of the fiber shaft region and the number of 15 amino-acid repeats differ between adenoviral serotypes. For example, the Ad2 fiber shaft is 37 nm long and contains 22 repeats, whereas the Ad3 fiber is 11 mn long and contains 6 repeats. The receptor binding domain of the fiber protein is localized in the knob region encoded by the last 200 amino acids of the protein (Henry et al.,*J. of Virology,* 68(8), 5239–5246 (1994)). The regions necessary for trimerization are also located in the knob region of the protein (Henry et al. (1994), supra). A deletion mutant lacking the last 40 amino acids does not trimerize and also does not bind to penton base (Novelli et al. *Virology,* 185, 365–376 (1991)). Thus, trimerization of the fiber protein is necessary for penton base binding. Nuclear localization signals that direct the protein to the nucleus to form viral particles following its synthesis in the cytoplasm are located in the N-terminal region of the protein (Novelli et al. (1991), supra). The fiber, together with the hexon, are the main antigenic determinants of the virus and also determine the serotype specificity of the virus (Watson et al.,*J. Gen. Virol.,* 69, 525–535 (1988)). The fiber protein is glycosylated with single N-acetyl-glucosamine residues; however, the functional significance of the glycosylation remains unclear (Caillet-Boudin et al., *Eur. J. Biochem.,* 184, 205–211 (1989)).

Over ten fiber proteins from different adenoviral serotypes have been sequenced, only to reveal a larger sequence diversity than that observed among other adenoviral proteins. For example, the knob regions of the fiber proteins from the closely related Ad2 and Ad5 serotypes are only 63% similar at the amino acid level (Chroboczek et al., *Virology,* 186, 280–285 (1992)), whereas their penton base sequences are 99% identical. Ad2 and Ad5 fiber proteins, however, both likely bind to the same cellular receptor, since they cross-block each other's binding. In contrast, Ad2 and Ad3 fibers are only 20% identical (Signas et al., *J. of Virology,* 53, 672–678 (1985)) and presumably bind to different receptors, since each fails to cross-block the other's binding (Defer et al., *J. of Virology,* 64(8), 3661–3673 (1990)). Ad3 fiber utilizes sialic acid as its receptor, whereas Ad2 fiber does not. Pretreatment of cells with neuraminidase or periodate abrogates Ad3, but not Ad2, binding. Also, soluble analogues of sialic acid block Ad3, but not Ad2, binding. However, sequence comparisons of the Ad2 and Ad3 fiber genes do show distinct regions of conservation. Most of these regions are also conserved in the other human adenoviral fiber genes. Nonhuman adenoviral fiber genes show less homology to human serotypes but still trimerize. The receptors used by nonhuman serotypes are unknown.

Recombinant adenoviral vectors have been used for the cell-targeted transfer of one or more recombinant genes to diseased cells or tissue in need of treatment. Such vectors are characterized by the advantage of not requiring host cell proliferation for expression of adenoviral proteins (Horwitz et al., In *Virology,* Raven Press, New York, vol. 2, pp.

1679–1721 (1990); and Berkner, *BioTechniques,* 6, 616 (1988)), and, if the targeted tissue for somatic gene therapy is the lung, these vectors have the added advantage of being normally trophic for the respiratory epithelium (Straus, *In Adenoviruses,* Plenan Press, New York, pp. 451–496 (1984)).

Other advantages of adenoviruses as potential vectors for human gene therapy are as follows:

(i) recombination is rare; (ii) there are no known associations of human malignancies with adenoviral infections despite common human infection with adenoviruses; (iii) the adenoviral genome (which is a linear, double-stranded DNA) can be manipulated to accommodate foreign genes that range in size; (iv) an adenoviral vector does not insert its DNA into the chromosome of a cell, so its effect is impermanent and unlikely to interfere with the cell's normal function; (v) the adenovirus can infect non-dividing or terminally differentiated cells, such as cells in the brain and lungs; and (vi) live adenovirus, having as an essential characteristic the ability to replicate, has been safely used as a human vaccine (Horwitz et al. (1990), supra; Berkner et al. (1988), supra; Straus et al. (1984), supra; Chanock et al., *JAMA,* 195, 151 (1966); Haj-Ahmad et al., *J. Virol.,* 57, 267 (1986); and Ballay et al., *EMBO,* 4, 3861 (1985)).

A drawback to adenovirus-mediated gene therapy is that significant decreases in gene expression are observed after two weeks following administration of the vector. In many therapeutic applications the loss of expression requires re-administration of the viral vector to overcome losses in expression. However, following administration of the viral vector, neutralizing antibodies are raised against both the fiber and hexon proteins (Wohlfart, *J. Virology,* 62, 2321–2328 (1988); Wohlfart et al., *J. Virology,* 56, 896–903 (1985)). This antibody response against the virus then can prevent effective re-administration of the viral vector. Accordingly, recombinant adenoviral vectors capable of avoiding such neutralizing antibodies that would allow repeated doses of adenoviral vectors to be administered in the context of gene therapy would represent a significant advance in current gene therapy methodology.

Another drawback of using recombinant adenovirus in gene therapy is that all cells that express the aforementioned two receptors used by adenovirus to attach and infect a cell will internalize the gene(s) being administered not just the cells in need of therapeutic treatment. Likewise, certain cells, such as lymphocytes, which lack the $\alpha_v$ integrin adenoviral receptors, are impaired in the uptake of adenoviruses (Silver et al., *Virology* 165, 377–387 (1988); Horvath et al., *J. of Virology,* 62(1), 341–345 (1988)) and are not readily amenable to adenovirus-mediated gene delivery. Accordingly, limiting adenoviral entry to specific cells or tissues and/or expanding the repertoire of cells amenable to adenovirus-mediated gene therapy would be a significant improvement over the current technology. Targeted adenoviral gene delivery should expand the cells amenable to gene therapy, reduce the amount of adenoviral vector that is necessary to obtain gene expression in the targeted cells, and reduce side effects and complications associated with increasing doses of adenovirus, such as inflammation and the transfection of normal, healthy cells.

Attempts have been made to target a virus to specific cells by sterically blocking adenoviral fiber protein with antibodies and chemically linking tissue-specific antibodies to the viral particle (Cotten et al., *Proc. Natl. Acad. Sci. USA,* 89, 6094–6098 (1992)). Although this approach has demonstrated the potential of targeted gene delivery, the complexity and reproducibility of this approach present major hurdles blocking its application in clinical trials. The difficulties thus far encountered in targeting the virus by these methods involve the method of synthesis required, which is to make major alterations in the viral particles following their purification. These alterations involve additional steps that covalently link large molecules, such as polylysine, receptor ligands and antibodies, to the virus (Cotten (1 992), supra; Wagner et al., *PNAS USA,* 89, 6099–6103 (1992)). The targeted particle complexes are not homogeneous in structure and their efficiency is sensitive to the relative ratios of viral particles, linking molecules, and targeting molecules used.

The present invention seeks to overcome at least some of the aforesaid problems of recombinant adenoviral gene therapy. In one aspect, the present invention provides a recombinant adenoviral vectors capable of avoiding neutralizing antibodies upon repeat administration, thereby enabling the maintenance of recombinant gene expression at a therapeutically effective level. The present invention also relates to a cell-specific/tissue-specific recombinant adenovirus so as to target gene therapy to selected cells/tissues, thereby reducing the amount of recombinant adenoviral vector administered and any side-effects/complications. In another embodiment, the present invention provides means for modifying the viral particle at the level of gene expression, thus allowing viral particles to be purified by conventional techniques. In another embodiment, the present invention provides a method of gene therapy involving the use of such a homogeneous adenovirus, without the need for additional chemical modifications of viral particles, such as psoralen inactivation, or the addition of molecules to the virus which permit the covalent linkage of additional molecules to the virus. These and other objects and advantages of the present invention, as well as additional inventive features, will be apparent from the following detailed description.

BRIEF SUMMARY OF THE INVENTION

The present invention provides a recombinant adenovirus comprising a chimeric fiber protein, which differs from the native (wild-type) fiber protein by the introduction of a nonnative amino acid sequence. The nonnative amino acid sequence allows the adenovirus to be targeted towards a protein, such as a receptor or a bi- or multi-specific protein, which is specific for binding to the nonnative amino acid sequence and a target receptor, by facilitating direct binding between the nonnative amino acid sequence and the protein, i.e., receptor or bi/multi-specific protein. Alternatively, the nonnative amino acid sequence facilitates proteolytic removal of the chimeric fiber protein to allow targeting of the adenovirus by means of another adenoviral coat protein, such as the penton base. The present invention also provides an adenoviral transfer vector, among others, comprising a recombinant fiber gene sequence for the generation of a chimeric fiber protein, and a method of using a protein-specific recombinant adenovirus, which is specific for a given receptor or bi-/multi-specific protein and which comprises a therapeutic gene, in gene therapy.

DETAILED DESCRIPTION OF THE INVENTION

Figure 1:
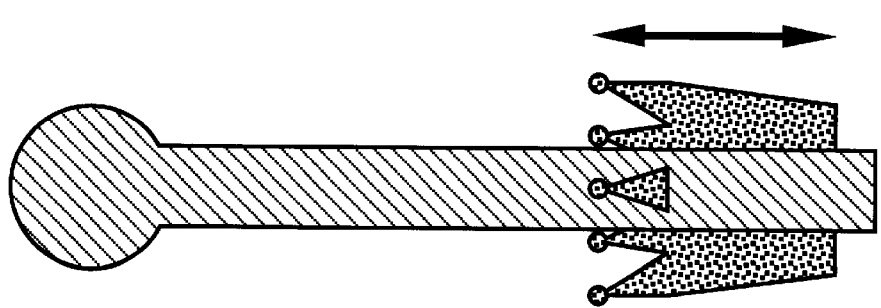
FIG. 1 is a diagram of the penton complex.

The present invention provides, among other things, a recombinant adenovirus comprising a chimeric fiber protein. The chimeric fiber protein comprises a nonnative amino acid sequence, in addition to or in place of a native fiber amino acid sequence, which allows the adenovirus to bind to a protein, such as a receptor, which is other than a receptor bound by the native fiber, and which is referred to herein as a "target receptor," or a bi-/multi-specific protein, such as an antibody or fragment thereof, e.g., domain, with binding specificity for the nonnative amino acid sequence and for a target receptor. In the absence of native fiber amino acid sequences that enable trimerization of the native or chimeric fiber protein, the nonnative amino acid sequence comprises one or more sequences that enable trimerization of the chimeric fiber protein, which preferably are not immediately adjacent to the sequence that is specific for the aforesaid different protein, e.g., target receptor or bi- or multi-specific protein. Alternatively, the chimeric fiber protein comprises a nonnative amino acid sequence, in addition to or in place of a native fiber amino acid sequence, which is recognized by a protease and is cleaved by the protease, effectively removing the chimeric fiber protein and thereby allowing targeting of the adenovirus by means of another adenoviral coat protein, such as the penton base.

By "nonnative amino acid sequence" is meant any amino acid sequence that is not found in the native fiber of a given serotype of adenovirus and which is introduced into the fiber protein at the level of gene expression. "Nonnative amino acid sequence" includes an amino acid sequence from an adenoviral serotype other than the serotype of the adenovirus with the chimeric fiber protein. (For example, an Ad3 fiber amino acid sequence or the entire Ad3 fiber expressed in an Ad5 chimeric fiber protein or in place of an Ad5 fiber protein, respectively, is a "nonnative amino acid sequence.") It also includes a protease recognition sequence, i.e., a sequence that is recognized and cleaved by a protease.

By "protein-specific amino acid sequence" is meant any nonnative amino acid sequence encoding a protein, protein domain or peptide, whether specifically bound by another protein or fragment thereof, and is meant to include an amino acid sequence that confers upon a chimeric fiber the ability to directly bind to a target receptor or class of target receptors, preferably a cell-specific or tissue-specific receptor, and an amino acid sequence that confers upon a chimeric fiber the ability to directly bind to a bi- or multi-specific protein, such as an antibody or fragment thereof, e.g., domain, which binds to a target receptor(s).

By "receptor" is meant a protein, including membrane-bound and soluble proteins, with high specific affinity for biologically active substances, such as hormones, antibodies, and enzymes.

By "chimeric fiber protein" is meant a fiber protein comprising a nonnative amino acid sequence, which comprises either a protein binding sequence or a protease recognition sequence, in addition to or in place of a native fiber amino acid sequence, which comprises a protein binding sequence. "Chimeric fiber protein" is intended to include a fiber protein of a serotype which differs from that of the adenovirus on which it is expressed, i.e., where the entire native fiber sequence is replaced with an entire nonnative fiber sequence.

Incorporation of a protein-specific amino acid sequence into a chimeric fiber molecule allows targeting through two or more separate proteins which are chemically or otherwise linked to make a bi- or multi-specific protein. One component of the bi- or multi-specific protein binds to the fiber chimera. The second component or additional components of the bi- or multi-specific protein recognize(s) one or more additional target receptors. For example, a bi- or multi-specific protein can include a bispecific multichain or single chain antibody (Cook et al., *J. Immunol. Methods,* 171, 227–237 (1994); Spooner et al., *Human Pathol.,* 25, 606–614 (1994)) in which one domain specifically binds an epitope on chimeric fiber protein and the other domain specifically binds a target receptor. The bispecific antibodies bind to the chimeric fiber proteins in a recombinant adenovirus with the target receptor-specific domains of the bispecific antibodies available for binding to a target receptor.

Preferably, the entire native fiber protein or native receptor binding sequence of the fiber protein has been replaced at the DNA level with a nonnative protein-specific amino acid binding sequence. Alternatively, the native receptor binding sequence in the fiber gene has been rendered inactive at the DNA level by mutation of the sequence, such as by insertional mutagenesis, for example, or rendered conformationally inaccessible in the fiber protein, such as by insertion of a DNA sequence into or adjacent to the adenoviral fiber gene sequence, wherein "gene sequence" refers to the complete fiber gene sequence as well as any lesser gene sequence that is capable of being expressed as a functional fiber protein. For insertional mutagenesis, the DNA sequence is preferably inserted near the gene sequence encoding the native receptor binding sequence, so as to move the gene sequence encoding the native receptor binding sequence within the fiber gene sequence such that, in the chimeric fiber protein, the native receptor binding sequence is conformationally inaccessible for binding to a receptor. In the latter case, the inserted nonnative gene sequence that causes the conformational inaccessibility of the native receptor binding sequence in the fiber protein is preferably one that is specific for a target receptor or bi- or multi-specific protein. Such a recombinant adenovirus can be used, for example, to study receptor binding, adenoviral attachment, and adenoviral infection in vitro or in vivo.

In a preferred embodiment of the present invention, the above-described recombinant adenovirus additionally comprises a gene or genes capable of being expressed in a cell to which the virus has attached or by which the virus has been internalized and preferably is one having therapeutic utility, e.g., corrective DNA, i.e., DNA encoding a function that is either absent or impaired, or a discrete killing agent, such as DNA encoding a cytotoxin that, for example, is active only intracellularly, or DNA encoding ribozymes or antisense molecules. Accordingly, the use of the term "therapeutic gene" is intended to encompass these and any other embodiments of that which is more commonly referred to as gene therapy and is known to those of skill in the art. The recombinant adenovirus can be used for gene therapy or to study the effects of expression of the gene in a given cell or tissue in vitro or in vivo.

The recombinant adenovirus comprising a chimeric fiber protein and the recombinant adenovirus that additionally comprises a gene or genes capable of being expressed in a particular cell can be generated by use of a viral transfer vector, preferably an adenoviral transfer vector, in accordance with the present invention. The viral transfer vector, preferably an adenoviral transfer vector, comprises a chimeric adenoviral fiber gene sequence. The chimeric fiber gene sequence comprises a nonnative gene sequence in place of a native fiber gene sequence that encodes a receptor binding sequence, which has been deleted, or in addition to a native receptor binding sequence, which has been mutated or rendered conformationally inaccessible in the expressed chimeric fiber protein as described above. The nonnative sequence renders the adenovirus specific for binding to a protein, e.g., a receptor or bi- or multi-specific protein, as described above and, in the absence of native trimerization sequences, contains a sequence(s) which allows the chimeric protein to trimerize. Alternatively, the nonnative sequence comprises an entire fiber sequence from an adenovirus of a different serotype, which is then expressed in place of or in conjunction with native fiber on a given adenovirus. In other words, either all of the fibers on a given chimeric serotype or some of the fibers are of the native serotype, whereas others are of a nonnative serotype. Another alternative is that the nonnative sequence comprises one or more of a protease recognition sequence, which is cleaved by a protease, thereby effecting removal of the chimeric fiber and targeting of the recombinant adenovirus by means of the penton base or other coat protein (see FIG. 1 for diagram of penton complex). Based upon the high degree of structural similarity between the fiber molecules of the more than 41 human serotypes of adenovirus, it is expected that any one of the serotypes of human or nonhuman adenovirus may be used as the source of the fiber gene. It is preferred, however, that one of the serotypes for which the fiber gene has been sequenced is used.

Restriction sites are introduced into the fiber gene sequence; preferably, such restriction sites are introduced into or flanking a native receptor binding sequence of the fiber gene sequence by a suitable method, such as PCR mutagenesis. Preferably, these restriction sites are not already present in the fiber gene. Such sites facilitate the removal or inactivation, such as by sequence alteration, of the DNA sequence encoding the native receptor binding sequence in a given adenoviral genome, or the rendering of the native receptor binding sequence conformationally inaccessible, thereby altering or eliminating the ability of the fiber to bind to a receptor normally bound by the fiber. A deleted native receptor binding sequence can be replaced with, or a mutated or conformationally inaccessible receptor binding sequence can be accompanied by, a different DNA sequence, preferably a DNA sequence encoding specificity for binding to a protein, such as a receptor, preferably a cell-specific or tissue-specific receptor, or class of receptors, or to a bi- or multi-specific protein with specificity for a given receptor, for example. Unique restriction sites in the fiber gene of one adenoviral serotype can be used to replace regions of the native fiber gene with homologous regions of the fiber gene from another serotype. Such restriction sites can even be used to replace an entire native fiber sequence with a nonnative fiber sequence.

Figure 10:
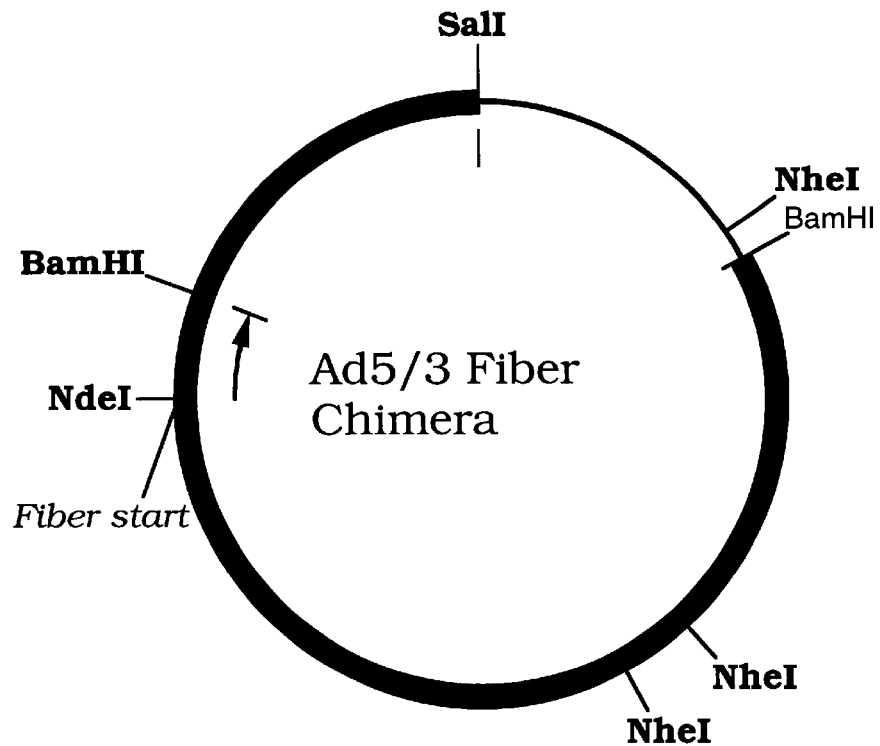
FIG. 10 is a partial restriction map of the vector pGBS.59–100 (F3).

Preferably, the adenoviral vector is one into which any suitable nonnative amino acid sequence can be rapidly inserted. For example, unique Nde I and Bam HI restriction sites in p 1 93 FC(F⁻) can be used to insert receptor binding sequences from other fiber serotype genes. Alternatively, sequences also can be inserted into the fiber gene sequence without the need for unique restriction sites through PCR. Because a recombinant adenovirus can be created via ligation of recombinant sequences with viral DNA or via homologous recombination, the adenoviral vector preferably has either (1) unique restriction sites that allow ligation of a vector fragment with the complementing fragments of the remaining viral genomes, as described in Example 1, or (2) adequate lengths of DNA on either side of the protein-specific sequence that allow efficient homologous recombination with viral DNA, as described in Example 1. A preferred adenoviral vector is shown in FIG. 10, which is a partial restriction map of such a vector. The adenoviral vector of FIG. 10 was generated as described in Example 1.

DNA encoding short peptide sequences or protein domains capable of binding to a given protein, preferably a receptor or class of receptors, in particular cell- or tissue-specific receptor, is preferred for insertion into the fiber gene sequence in which the native receptor binding sequence has been deleted, mutated, or rendered conformationally inaccessible. However, other DNA sequences, such as those that encode bi-/multi-specific protein recognition sequences, such as receptor-specific antibody domains and sequences that encode antigenic epitopes recognized by specific antibodies, also may be used to replace the native receptor binding sequence. The target receptor is optimally cell-specific or tissue-specific, and desirably is expressed only on those cells or tissues to be treated.

A non-native, unique protease site also can be inserted into the fiber gene sequence to target an adenovirus through the penton base or penton base chimeras. The protease site preferably does not affect fiber trimerization or receptor specificity of the fiber protein. The fiber chimera—containing particles are produced in standard cell lines, e.g., those currently used for adenoviral vectors. Following production and purification, the particles are rendered fiberless through digestion of the particles with a sequence-specific protease, which cleaves the fiber proteins and releases them from the viral particles to generate fiberless particles. For example, thrombin recognizes and cleaves at the amino acid sequence Val Pro Arg Gly Ser (TRINS) (SEQ ID NO: 8) (Stenflo et al., *J. Biol Chem.*, 257, 12280–12290 (1982)). Fiberless particles have been shown to be stable and capable of binding and infecting cells (Falgout et al., *J. of Virology*, 62, 622–625 (1992)). These resultant particles then can be targeted to specific tissues via the penton base or other coat protein.

The size of the DNA used to replace the native receptor binding sequence may be constrained, for example, by impeded folding of the fiber or improper assembly of the penton base/fiber complex.

Alternatively, recombinant adenovirus comprising chimeric fiber protein may be produced by the removal of the native knob region, which comprises receptor-binding and trimerization domains, of the fiber protein and its replacement with a nonnative trimerization domain and a protein-specific binding domain (Peteranderl et al., *Biochemistry*, 31, 12272–12276 (1992)). A recombinant adenovirus comprising a chimeric fiber protein also may be produced by point mutation in the knob region and the isolation of clones that are capable of trimerization but incapable of binding to the native receptor. In either case, and also with respect to the removal and replacement of the native receptor-specific binding sequence as described above, new protein binding domains may be added onto the C-terminus of the fiber protein or into exposed loops of the fiber protein by inserting the nucleic acid sequence encoding the binding domain into the fiber gene sequence at the appropriate position.

Irrespective of which method is used to introduce a protein binding sequence into the fiber protein, the fiber protein must be able to trimerize. If the fiber protein cannot trimerize, it will be unable to bind to penton base protein. Accordingly, the native receptor binding sequence must be changed without affecting the ability of the molecule to trimerize.

A recombinant chimeric fiber gene sequence can be moved from an adenoviral transfer vector into baculovirus or a suitable prokaryotic or eukaryotic expression vector for expression and evaluation of receptor or protein specificity and avidity, trimerization potential, penton base binding, and other biochemical characteristics. Accordingly, the present invention also provides recombinant baculoviral and prokaryotic and eukaryotic expression vectors comprising a chimeric adenoviral fiber gene sequence. The chimeric fiber gene sequence includes a nonnative sequence in addition to or in place of a native fiber amino acid sequence, which is specific for binding to a protein other than a protein bound by the native fiber. The native fiber amino acid sequence may be deleted, mutated, or rendered conformationally inaccessible as described above with respect to the recombinant adenovirus comprising a chimeric fiber protein. By moving the chimeric gene from an adenoviral vector to baculovirus or a prokaryotic or eukaryotic expression vector, high protein expression is achievable (approximately 5–50% of the total protein being the chimeric fiber). Accordingly, the present invention also provides a recombinant baculovirus comprising a chimeric fiber gene and a chimeric adenoviral fiber protein comprising a nonnative amino acid sequence in addition to or in place of a native fiber amino acid sequence. The nonnative amino acid sequence is specific for binding to a protein, such as a receptor or a bi-/multi-specific protein, or encodes a protease cleavage site as described above. For protein characterization studies, the recombinant chimeric fiber protein (rcF protein, such as rcF5) can be purified using any suitable methods, such as those described by Wickham et al. (1993), supra.

Various characteristic parameters of the fiber protein of interest can be assessed. Specificity and affinity of the receptor or other protein/rcF interaction can be assessed by Scatchard analysis as shown previously by Wickham et al. (1993), supra, for wild-type penton base protein. Receptor specificity can be further assessed by using antibodies and peptides specific for the targeted receptor to block rcF5 binding to cells, using conventional methods. rcF binding to penton base protein can be assessed by its ability to precipitate radiolabeled penton base protein when coupled to protein A-coated beads via an antibody to the fiber protein.

Viral attachment, entry and gene expression are evaluated initially by using the adenoviral vector containing the insert of interest to generate a recombinant virus expressing the chimeric fiber protein and a marker gene, such as $\beta$-galactosidase. $\beta$-galactosidase expression in cells infected with adenovirus containing the $\beta$-galactosidase gene (Ad-LacZ) can be detected as early as two hours after adding Ad-Gluc to cells. This procedure provides a quick and efficient analysis of cell entry of the recombinant virus and gene expression, and is implemented readily by an artisan of ordinary skill using conventional techniques.

A recombinant virus, which lacks a native receptor binding sequence in the fiber, can be produced in human embryonic cell line 293 (HEK 293), which allows replication of Ad5LacZ virus in which the LacZ gene replaces the E1 region of the adenoviral genome. For producing recombinant adenovirus containing chimeric fiber, the 293 cell line must express the receptor to which the chimeric fiber protein is targeted. In the absence of constitutive receptor expression, the receptor gene can be transfected into the 293 cell line to create a stably expressing cell line.

Recombinant adenoviruses of the present invention can be used to treat any one of a number of diseases by delivering to targeted cells corrective DNA, i.e., DNA encoding a function that is either absent or impaired, or a discrete killing agent, e.g., DNA encoding a cytotoxin that, for example, is active only intracellularly. Diseases that are candidates for such treatment include, for example, cancer, e.g., melanoma, glioma or lung cancers; genetic disorders, e.g., cystic fibrosis, hemophilia or muscular dystrophy; pathogenic infections, e.g., human immunodeficiency virus, tuberculosis or hepatitis; heart disease, e.g., preventing restenosis following angioplasty or promoting angiogenesis to reperfuse necrotic tissue; and autoimmune disorders, e.g., Crohn's disease, colitis or rheumatoid arthritis.

One skilled in the art will appreciate that suitable methods of administering a recombinant adenovirus of the present invention to an animal for purposes of gene therapy (see, for example, Rosenfeld et al., *Science*, 252, 431–434 (1991); Jaffe et al., *Clin. Res.*, 39(2), 302A (1991); Rosenfeld et al., *Clin. Res.*, 39(2), 311A (1991); Berkner, *BioTechniques*, 6, 616–629 (1988)), chemotherapy, and vaccination are available, and, although more than one route can be used to administer such a recombinant adenovirus, a particular route can provide a more immediate and more effective reaction than another route. Pharmaceutically acceptable excipients are also well-known to those who are skilled in the art, and are readily available. The choice of excipient will be determined in part by the particular method used to administer the recombinant adenovirus. Accordingly, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The recombinant adenovirus of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the recombinant adenovirus of the present invention may be made into suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, the dose should be sufficient to effect a therapeutic response.

In addition to the recombinant adenovirus of the present invention, the recombinant vectors, e.g., the adenoviral transfer vector, also have utility in vitro. They can be used as a research tool in the study of adenoviral attachment and infection of cells and in a method of assaying receptor-ligand interaction. Similarly, the recombinant fiber protein comprising a nonnative amino acid sequence in addition to or in place of a native receptor binding sequence can be used in receptor-ligand assays and as adhesion proteins in vitro or in vivo, for example.

The following examples further illustrate the present invention and, of course, should not be construed as in any way limiting its scope.

EXAMPLE 1

This example describes how to change adenoviral antigenicity without changing receptor specificity by creating a chimeric fiber protein in which the native Ad5 receptor binding domain is replaced with the nonnative Ad2 receptor binding domain.

Figure 4:
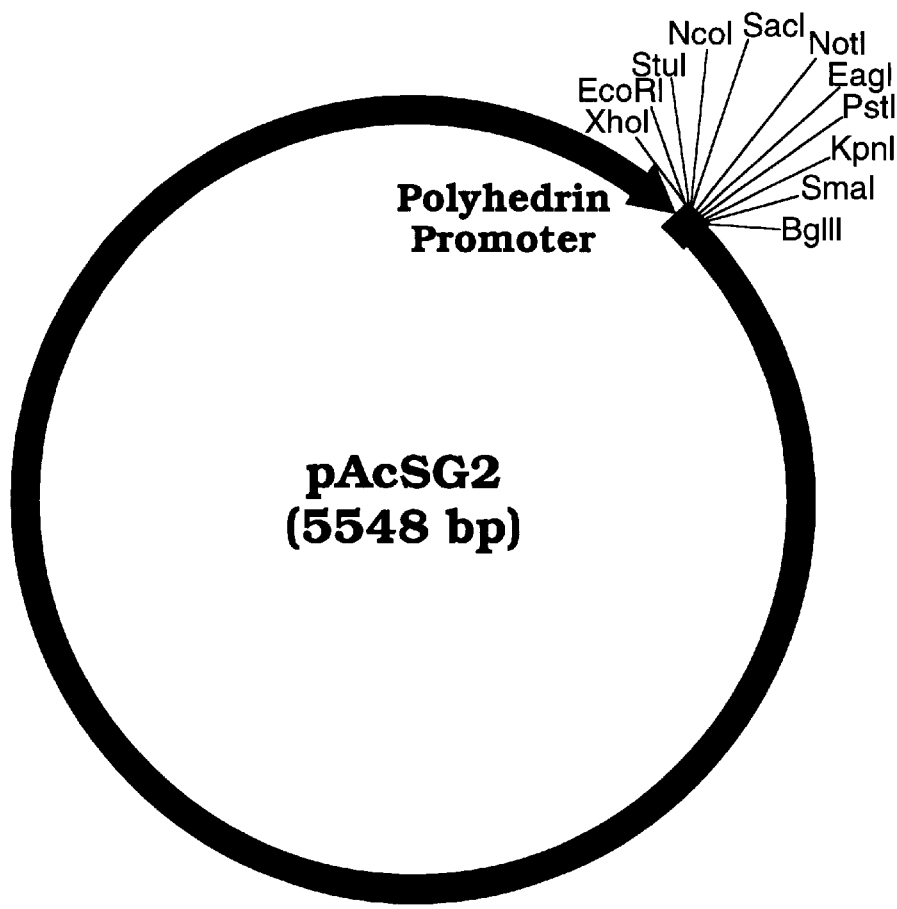
FIG. 4 is a partial restriction map of the vector pAcSG2.
Figure 8:
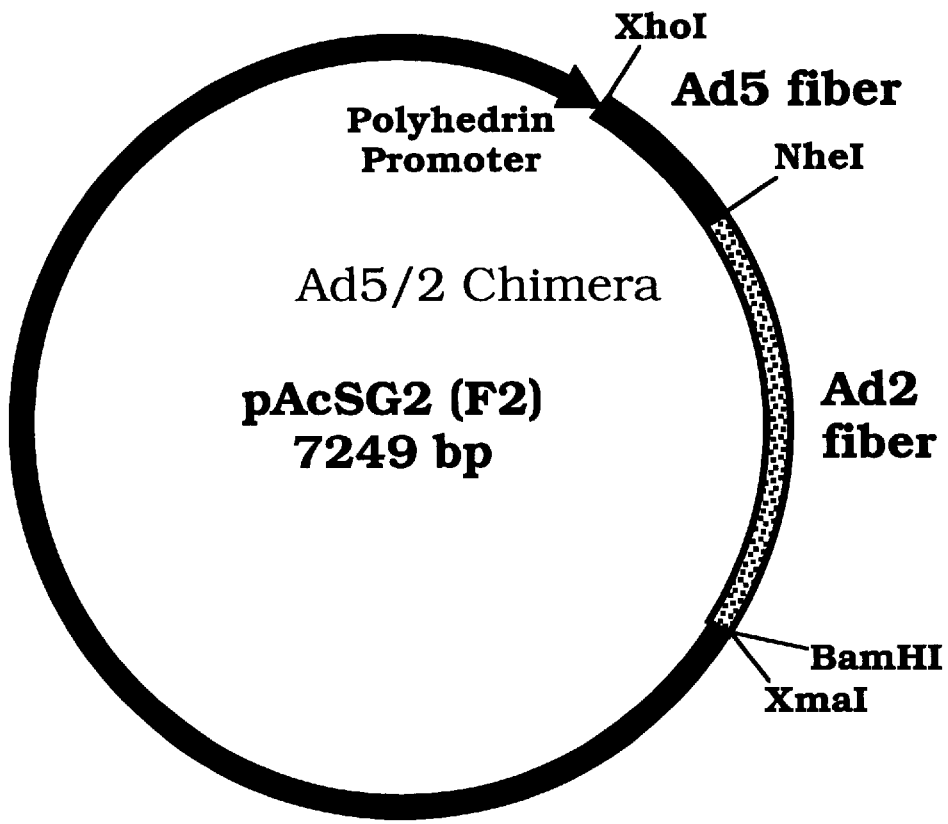
FIG. 8 is a partial restriction map of the vector pAcSG2 (F2).

The Ad2 fiber gene was amplified by PCR, wherein an Xho I site was incorporated into the 5' end of the sense PCR primer of SEQ ID NO: 1, and Xma I and Bam HI sites were incorporated into the 5' end of the antisense primer of SEQ ID NO:2 to allow cloning into the Xho I/Xma I cloning sites in the vector pAcSG2 (FIG. 4) (Pharmingen, San Diego, Calif.) to create the vector pAcSG2 (F2) (FIG. 8). The pAcSG2 (F2) was used to evaluate the fiber chimera at the protein level for receptor and penton base binding activity.

Figure 2:
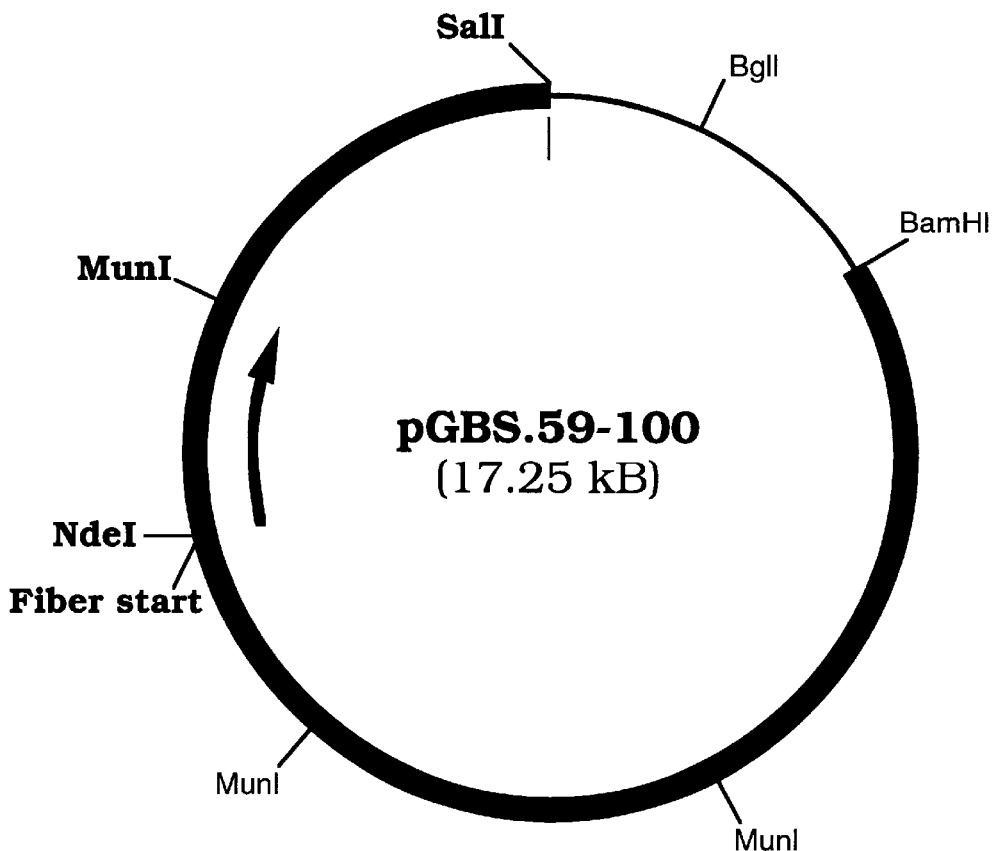
FIG. 2 is a partial restriction map of the vector pGBS.59–100.
Figure 3:
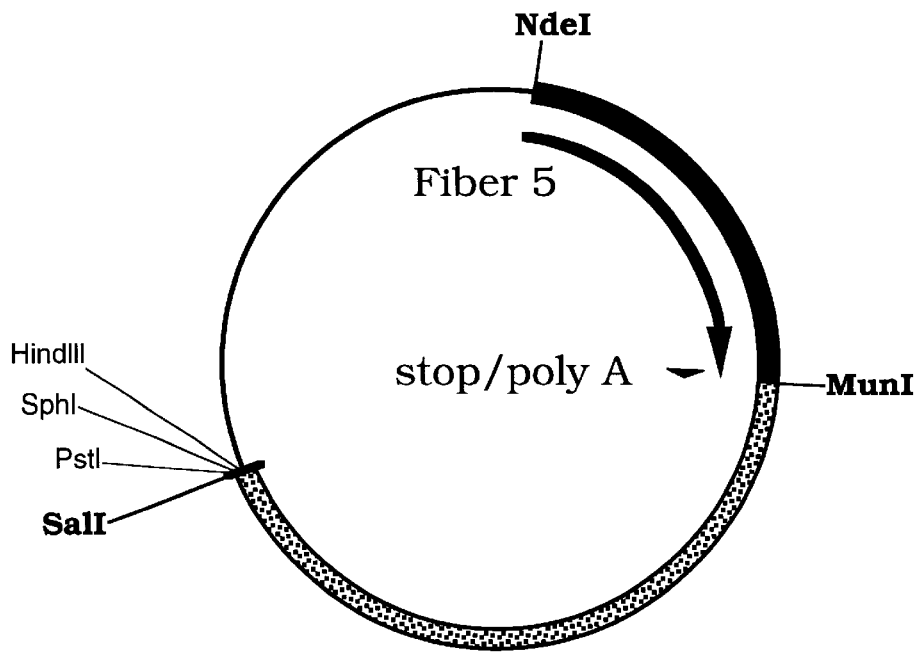
FIG. 3 is a partial restriction map of the vector p193 Ad5 Nde I/Sal I.
Figure 5:
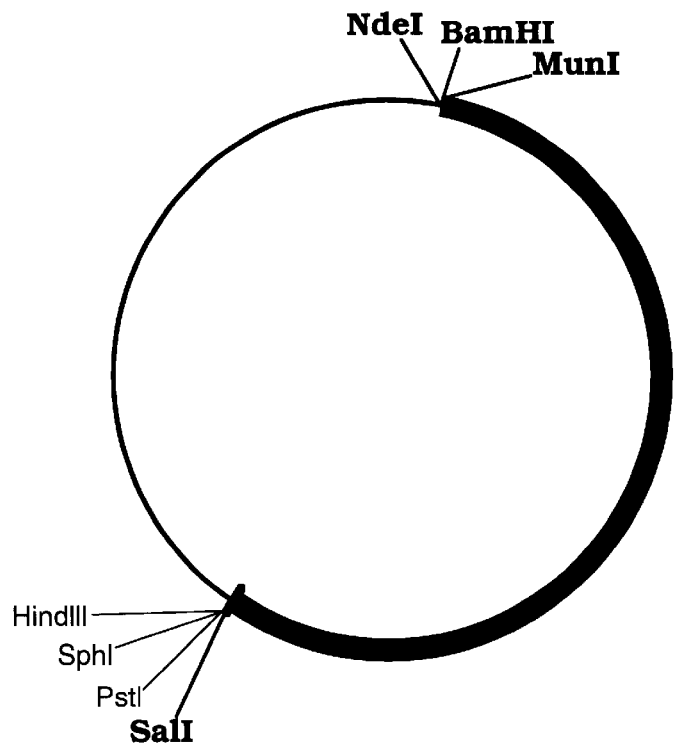
FIG. 5 is a partial restriction map of the vector p193 Ad5 FC (F–).
Figure 6:
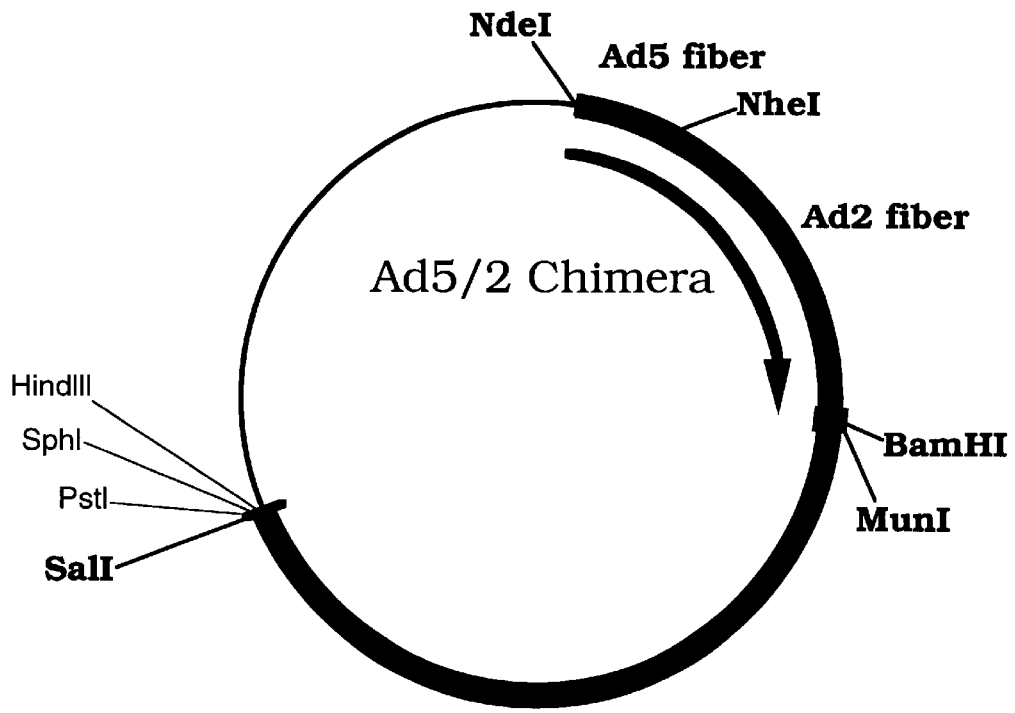
FIG. 6 is a partial restriction map of the vector p193 FC (F2).
Figure 7:
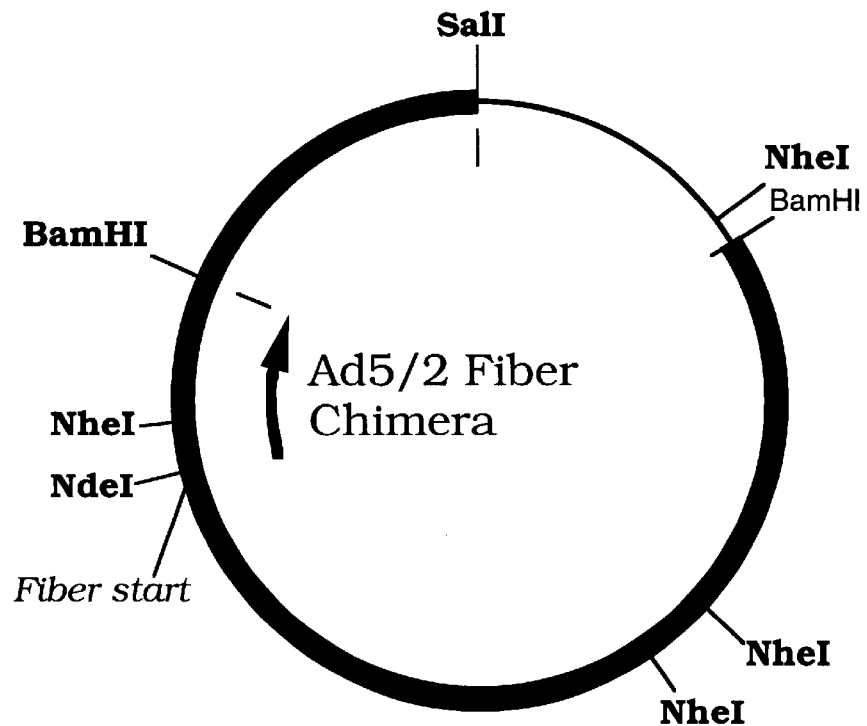
FIG. 7 is a partial restriction map of the vector pGBS.59–100 (F2).

The Nde I/Bam HI fragment of the fiber2 gene was removed from pAcSG2 (F2) and cloned into the vector p193 FC (F−) (FIG. 5) to create p193 FC (F2) (FIG. 6). The vector p193 FC (F−) was used as the base vector for making all chimeric fiber adenoviruses. The p193 FC (F−) vector was created by cutting the p193 Ad5 (Nde I/Sal I) (FIG. 3) vector with Nde I and Mun I to remove most of the Ad5 fiber gene, including its stop and polyadenylation signals, and by replacing the Nde I/Mun I fragment with a synthetic oligonucleotide, which lacks the amino acid coding region for Ad5 fiber but retains the Ad5 fiber stop and polyadenylation signal. The synthetic oligonucleotide was prepared from two sense and antisense complementary oligonucleotides, SEQ ID NO:3 and SEQ ID NO:4, respectively, which recreate cut Nde I and Mun I sites when paired and contain a Bam HI site just upstream of the stop codon to allow directional cloning into the Nde I/Bam HI sites. The Nde I/Sal I fragment containing the chimeric Ad2/Ad5 fiber gene was then cloned into the vector pGBS.59–100 (FIG. 2) to create the transfer vector pGBS.59–100 (F2) (FIG. 7). The pGBS.59–100 (F2) transfer vector was then cut with Sal I, purified and transfected into an appropriate cell line with a complementing 27,530 bp Ad5 DNA fragment (left arm, 0–27,530 bp) to create recombinant virus through homologous recombination. An appropriate cell line is any cell line which expresses the receptor for the chimeric fiber and which is capable of replicating the adenoviral vector. The complementing fragment of Ad5 DNA was prepared by cutting the Ad5 DNA with the restriction enzyme SrfI, which cuts the Ad5 genome once at position 27,530 in the wild-type Ad5 genome. The larger 27,530 bp piece was then isolated from the smaller bp fragment using a CsCl gradient, although an agarose gel or other appropriate separation technique could have been utilized.

Alternatively, viral DNA can be cut with a restriction enzyme, such as Spe I, which cuts at position 27,082 in the wild-type Ad5 genome. The 27,082 bp Spe I fragment can be isolated from the smaller fragment as described above and then ligated with the complementing Spe I/Sal I fragment from the pGBS.59–100 (F2) vector and then transfected into the appropriate cell line. Recombinant virus then can be isolated by plaque assay and verified as recombinant using PCR probes specific for the chimera and by restriction analysis.

EXAMPLE 2

This example describes how to change receptor specificity and antigenicity by creating a chimeric fiber protein in which the native Ad5 receptor binding domain is replaced with the nonnative Ad2 receptor binding domain.

Figure 9:
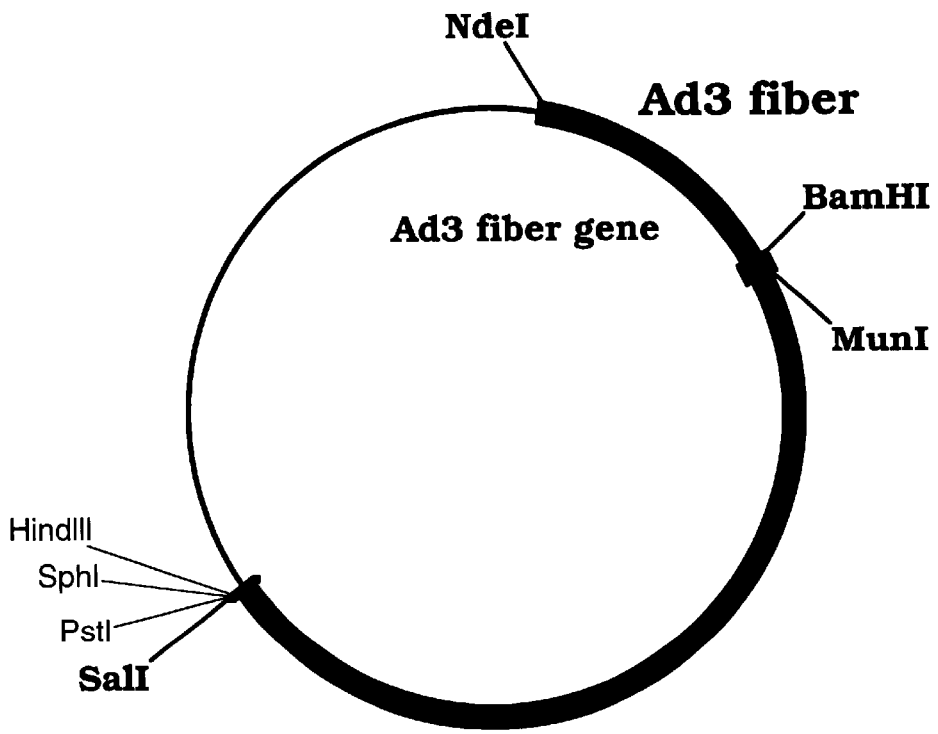
FIG. 9 is a partial restriction map of the vector p193 FC (F3).
Figure 11:
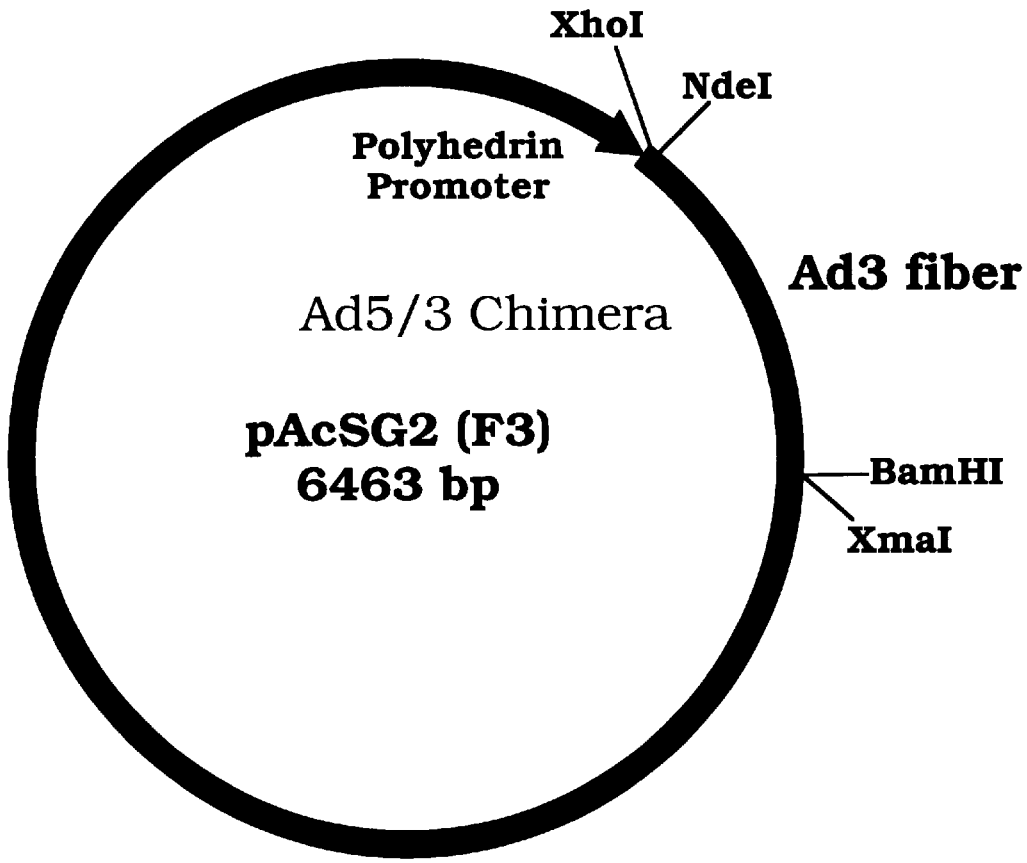
FIG. 11 is a partial restriction map of the vector pAcSG2 (F3).

Oligonucleotide primers were used to amplify a large fraction of the Ad3 fiber gene using PCR. The 5' sense primer of SEQ ID NO:5 contained an in-frame mutation that incorporated an Nde I site, whereas the antisense oligonucleotide of SEQ ID NO:6 incorporated a Bam HI site to allow cloning of the amplified fragment into pAcSG2 (F2) in which the corresponding Nde I/Bam HI region of the Ad2 fiber gene was removed. The Nde I/Bam HI fragment of the gene for Ad3 fiber was then removed from the vector pAcSG2 (F3) (FIG. 11) and cloned into the vector p193 FC (F−) to create p193 FC (F3) (FIG. 9). The Nde I/Sal I fragment containing the chimeric Ad3/Ad5 fiber gene was then cloned into the vector pGBS.59–100 to create the transfer vector pGBS.59–100 (F3) (FIG. 10). The pGBS.59–100 (F3) transfer vector was then cut, purified, and transfected into the appropriate cell line with Ad5 arms as in Example 1. Recombinant virus was then isolated and verified to be recombinant as in Example 1.

The receptor for Ad3 contains a sialic acid component, which is required for binding of Ad3, while binding of Ad5 does not involve sialic acid. Since sialic acid is found on all higher eukaryotic cells, the Ad3/Ad5 fiber chimera is capable of binding to all cells. Such a vector can infect a broader range of cell types and exhibits different tissue specificity than non-chimeric Ad5 vectors in vivo.

EXAMPLE 3

This example describes how receptor specificity can be changed and binding domains can be incorporated at the C-terminus of mouse adenoviral fiber.

The fiber sequence from a nonhuman adenoviral serotype, mouse adenovirus type 1, for example, is amplified using PCR. Nhe I and Bam HI sites incorporated into the sense and antisense PCR primers, respectively, allow subsequent cloning of the PCR product. The Nhe I site corresponds to a naturally occurring site in Ad5 fiber that occurs after the sequence encoding penton base recognition domains. The antisense primer, in addition to the required Bam HI site, contains a sequence encoding an $\alpha_v\beta_3$-specific RGD peptide following an amino acid spacer of 5–30 amino acids (such as poly [Ala Ser] or poly [Gly]). A unique restriction site is incorporated into the sequence following the spacer sequence and then again before the stop codon. The site allows the incorporation of receptor-specific sequences other than the $\alpha v\beta_3$-specific RGD peptide. The resultant PCR product is then cloned into pAcSG2 (F5) to replace the corresponding Ad5 fiber sequence and create pAcSG2 (MouseRGD). The Nde I/Bam HI fragment containing the chimeric fiber gene is cloned into p193 FC (F−) to create p193 FC (MouseRGD). The Nde I/Sal I fragment from p193 FC (MouseRGD) is cloned into pGBS.59–100 to create the transfer vector pGBS.59–100 (MouseRGD). The transfer vector is then prepared and transfected along with complementing Ad5 DNA into cells expressing the avb3 receptor as described in Example 1. Recombinant virus containing the chimeric fiber gene is analyzed as in Example 1. Using the unique restriction site incorporated into the vector, other receptor binding domains, such as the P-selectin binding domain or a single chain receptor-specific antibody, can be directly cloned into the vector. However, the cell line used for transfection must express the targeted receptor in order for the recombinant virus to attach and infect cells. Incorporation of receptor or antibody binding domains into fiber molecules that do not recognize human receptors allow for the targeting of a vector using such a fiber without retaining residual amino acid sequences that recognize human receptors and prevent efficient targeting.

EXAMPLE 4

This example describes how to change receptor specificity by mutating a native fiber receptor-binding domain and incorporating a nonnative binding domain at the C-terminus or within an exposed loop of a mutant Ad5. A mutated fiber gene, one which generates fiber that can trimerize but cannot bind to a native fiber receptor, is amplified by PCR using primers that incorporate proper restriction sites for cloning. The antisense primer, in addition to the required Bam HI site, contains a sequence encoding an $\alpha_v\beta_3$-specific RGD peptide following an amino acid spacer of 5–30 amino acids, such as poly (Ala Ser) or poly Gly. A unique restriction site is incorporated into the sequence following the spacer sequence and then before the stop codon. The site allows the incorporation of receptor-specific sequences other than the $\alpha_v\beta_3$-specific RGD peptide. The amplified chimeric gene is cloned into the p193 FC (F−) plasmid to obtain p193 FC (F5*:β3). The Nde I/Sal I fragment containing the chimeric fiber gene is then cloned into the pGBS.59–100 vector to obtain pGBS.59–100 (F5*:β3). The transfer vector is prepared and transfected with complementing Ad5 DNA as described in Example 1. Recombinant virus containing the chimeric fiber gene is analyzed as in Example 1. Other receptor-specific or antibody-specific binding domains can be cloned into the vector to create fiber chimeras with such sequences at the C-terminus of the protein or within exposed loops of the fiber molecule for targeting to other receptors or antibodies, respectively, as described in Example 3.

EXAMPLE 5

This example describes replacement of a knob with a trimerization domain and the incorporation of a binding domain at the C-terminus of the knob protein.

Figure 12:
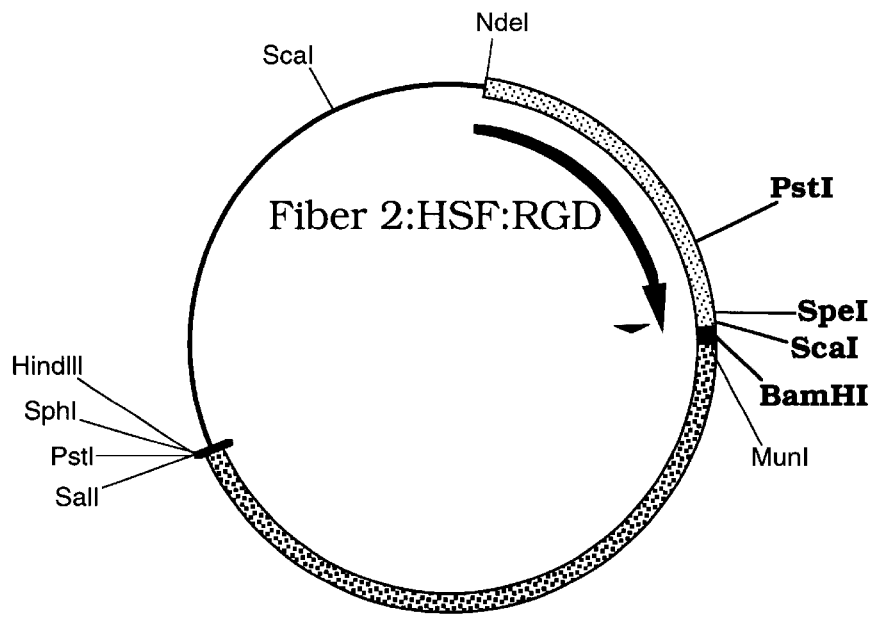
FIG. 12 is a partial restriction map of the vector p193 FC (HSF:RGD).
Figure 13:
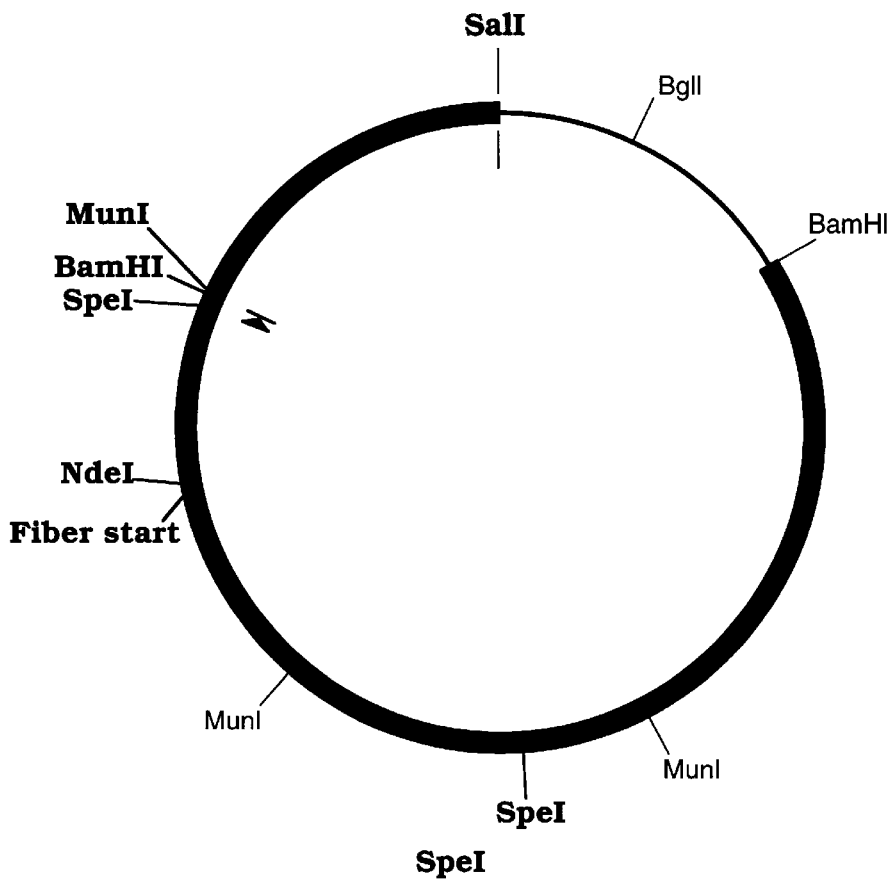
FIG. 13 is a partial restriction map of the vector pGBS.59–100 (HSF:RGD).
Figure 14:
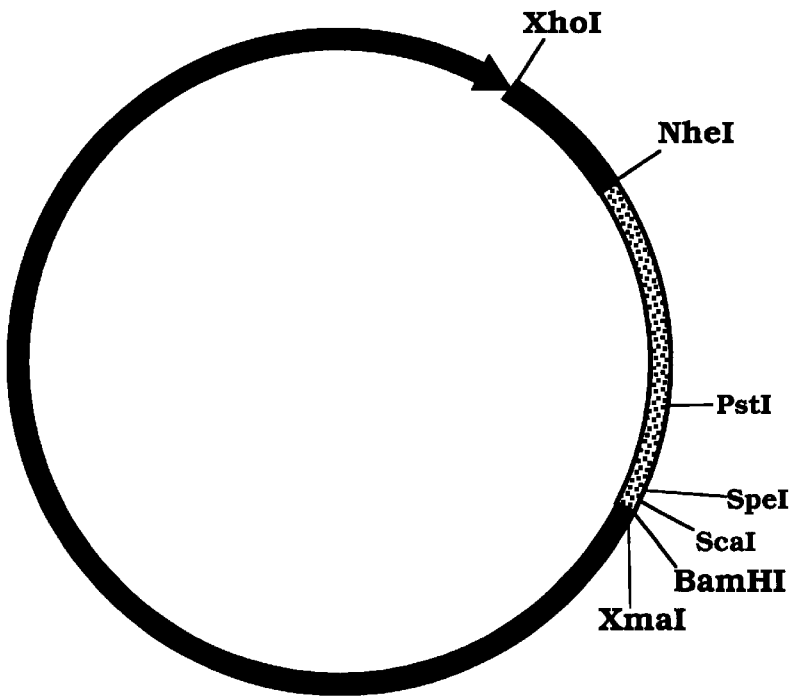
FIG. 14 is a partial restriction map of the vector pAcSG2 (HSF:RGD).
Figure 15:
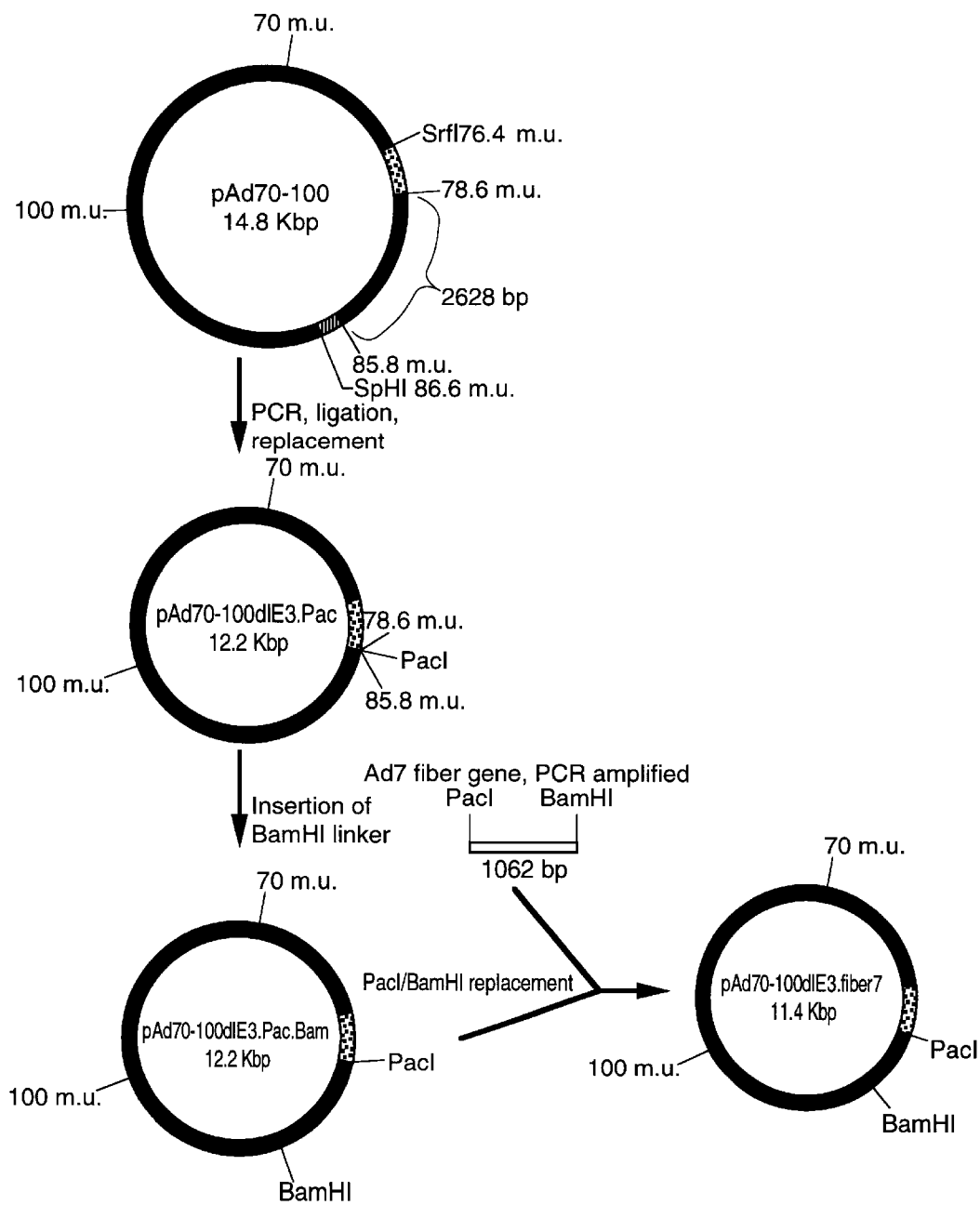
FIG. 15 is a diagram of the construction of the vector pAd70–100d1E3.fiber7.

The adenovirus type 2 fiber gene was amplified using PCR from Ad2 viral NA and cloned into the baculovirus transfer vector, pBlueBac2 (Invitrogen, La Jolla, Calif.), to generate the vector pBB2F. The unique restriction sites Pst I and Bam HI encompass the region of the fiber2 gene encoding the knob region of the protein. These sites were used to remove the Pst I to Bam HI portion of the fiber gene and to replace it with DNA encoding the trimerization domain from the heat shock factor (HSF) protein of *K. lactis* fused via a glycine spacer to an RGD peptide specific for the integrin avb3. The DNA encoding the HSF domain and RGD peptide was obtained through PCR from a plasmid containing the sequence for the entire *K. lactis* HSF protein. The DNA sequence encoding the RGD peptide was incorporated into the antisense DNA primer of SEQ ID NO:7 used in the PCR of the HSF trimerization domain to create the DNA sequence encoding the HSF:RGD fusion protein. The sense primer contained a Pst I site native to the Ad2 fiber gene. The PCR product was then digested with Pst I and Bam HI and cloned into the pAcSG2 (F2) vector to obtain the plasmid pAcSG2:HSF:RGD (FIG. 14). Unique Spe I and Sca I sites were incorporated into the chimeric HSF:RGD gene so that different receptor-specific or antibody-specific sequences could be rapidly inserted into the gene in place of the RGD-coding sequence at the end of the sequence encoding the glycine spacer arm. The pAcSG2:HSF:RGD plasmid (FIG. 14) was used to make recombinant baculovirus which expresses the fusion protein at high levels. The fusion protein expressed was the correct size and formed a trimer. The Nde I/Bam HI fragment of the chimeric gene was then removed from the vector pAcSG2 (HSF:RGD) and cloned into the vector p193 FC (F−) to create p193 FC (HSF:RGD) (FIG. 12). The Nde I/Sal I fragment containing the chimeric fiber gene was cloned into the vector pGBS.59–100 (FIG. 2) to create the transfer vector pGBS.59–100 (HSF:RGD) (FIG. 13). The pGBS.59–100 (HSF:RGD) transfer vector was then cut, purified and transfected into the appropriate cell line with Ad5 arms as in Example 1. Recombinant virus was then isolated and verified to be recombinant as in Example 1.

EXAMPLE 6

This example describes how to replace a knob with a trimerization domain and how to incorporate a binding domain containing a protease cleavage site at the C-terminus of the knob.

A chimeric fiber can be targeted to a new receptor by incorporating an epitope into the chimera which is recognized by a bi-specific antibody. An additional RGD domain is incorporated at the C-terminus of the protein and separated from the antibody epitope by a unique protease recognition site. The chimeric virus is capable of growing in tissue culture cells that express the receptor for the RGD sequence. Final preparations of virus are then exposed to the protease to remove the RGD sequence, leaving the epitope. The viral particles are then exposed to a bi-specific antibody in which one half of the molecule recognizes the epitope on the chimeric fiber and the other half recognizes any desired receptor, e.g., cell- or tissue-specific, receptor. The RGD sequence is absent and the virus binds to and enters only those cells recognized by the bi-specific antibody.

EXAMPLE 7

This example describes how to change the adenoviral antigenicity and receptor specificity of an Ad5 virus by replacing native Ad5 fiber with nonnative Ad7 fiber and demonstrates the ability of such recombinant virus to infect cells in vitro and in vivo.

The Ad5 virus —Ad7 fiber construct was generated as shown in FIG. 15. An approximately 2.7 kb (Ad5 28689–31317 bp) fragment in pAd7–100 was replaced with a Pac I linker (pAd70–100d1E3.Pac). A Bam HI linker was inserted at a unique Mun I site as indicated in FIG. 13 to produce pAd70–100d1E3.Pac.Bam. A PCR-amplified Pac I-Bam HI fragment of approximately 1.1 kb containing the Ad7 fiber gene was inserted into pAd70–100d1E3.Pac.Bam to produce pAd70–100d1E3.fiber7.

In order to assess the ability of Ad5 virus with Ad7 fiber to infect cells in vitro and in vivo, reporter gene assays were performed. A replication-defective recombinant adenoviral reporter vector designated AdCMV-CATNeo was used in the reporter gene assay. The reporter vector consists of the adenoviral origin of replication and viral packaging sequences, a combination of strong eukaryotic promoter (cytomegalovirus or CMV-1) and splicing elements, the bacterial chloramphenicol acetyl transferase (CAT) gene sequence, the mouse $\beta^{maj}$-globin poly(A) site, the neomycin gene sequence (Neo), and sufficient adenoviral DNA to allow for overlap recombination.

The reporter vector was used to generate AdCMV-CATNeo, AdCMV-CATNeo-d1E3 (AdCMV-CATNeo+pAd70–100d1E3) and AdCMV-CATNeo-d1E3-Fiber7 (AdCMV-CATNeo+pAd70–100d1E3.Fiber7) viruses. Each virus was grown in large scale, i.e., a 1 1 suspension of human embryonic kidney 293 cells, to yield virus at a concentration of $10^{12}$ particles/ml. A549 cells were infected with an estimated 100, 300 or 1,000 particles/cell of one of the three viruses. After 48 hr, the cells were harvested and lysates were prepared as described in Kass-Eisler et al., PNAS USA, 90, 11498–11502 (December 1993). Using 50 $\mu$lof each lysate, CAT assays were performed and acetylated chloramphenicol products were separated by thin layer chromatography using chloroform:methanol (95:5). The results of the assays indicated that each virus was able to infect cells and express gene products at appropriate levels. Accordingly, the virus in which the native fiber was replaced with a nonnative fiber could infect cells and express genes like the parental virus.

Following this study, adult Sprague Dawley rats were infected with $10^8$ viral particles by direct cardiac injection as described in Kass-Eisler et al, supra. Five days later, the rats were sacrificed, cardiac lysates were prepared, and CAT assays were performed. The amount of the CAT gene product produced was compared between the d1E3 and d1E3-Fiber 7 viruses. Results indicated that both viruses were able to infect cells in vivo. The replacement of the wild-type Ad5 fiber gene with that of Ad7 did not impair the ability of the virus to infect cells. Accordingly, the virus in which the native fiber was replaced with a nonnative fiber could also infect cells and express genes like the parental virus in vivo. These results support the utility of adenovirus with chimeric fiber in the context of gene therapy.

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

---

What is claimed is:

1. A chimeric adenovirus fiber protein lacking a native amino acid receptor-binding sequence, having a native trimerization domain, and comprising a nonnative amino acid sequence (a) joined to the chimeric adenovirus fiber protein by at least one spacer sequence or (b) inserted into an exposed loop of the chimeric adenovirus fiber protein, wherein the protein trimerizes when produced in a mammalian cell and binds to a receptor which is not bound by a native adenovirus fiber.

2. The chimeric adenovirus fiber protein of claim 1, wherein the native amino acid receptor-binding sequence is destroyed by insertional mutagenesis.

3. The chimeric adenovirus fiber protein of claim 1, wherein the nonnative amino acid sequence comprises a protein-specific amino acid sequence.

4. An adenoviras comprising the chimeric adenovirus fiber protein of claim 1.

5. The adenovirus of claim 4, wherein the adenovirus is targeted via an adenovirus penton protein, and wherein the adenovirus is not targeted via the chimeric adenovirus fiber protein.

6. The chimeric adenovirus fiber protein of claim 1, wherein the nonnative amino acid sequence is joined to the chimeric adenovirus fiber protein by at least one spacer sequence.

7. The chimeric adenovirus fiber protein of claim 1, wherein the nonnative amino acid sequence is inserted into an exposed loop of the chimeric adenovirus fiber protein.

8. A trimer comprising the chimeric adenovirus fiber protein of claim 1.

9. An isolated or purified nucleic acid that encodes the chimeric adenovirus fiber protein of claim 1.

10. The chimeric adenovirus fiber protein of claim 6, wherein the native amino acid receptor-binding sequence is destroyed by insertional mutagenesis.

11. The chimeric adenovirus fiber protein of claim 6, wherein the nonnative amino acid sequence comprises a protein-specific amino acid sequence.

12. An adenovirus comprising the chimeric adenovirus fiber protein of claim 6.

13. The adenovirus of claim 12, wherein the adenovirus is targeted via an adenovirus penton protein, and wherein the adenovirus is not targeted via the chimeric adenovirus fiber protein.

14. A trimer comprising the chimeric adenovirus fiber protein of claim 6.

15. An isolated or purified nucleic acid that encodes the chimeric adenovirus fiber protein of claim 6.

16. The chimeric adenovirus fiber protein of claim 7, wherein the native amino acid receptor-binding sequence is destroyed by insertional mutagenesis.

17. The chimeric adenovirus fiber protein of claim 7, wherein the nonnative amino acid sequence comprises a protein-specifc amino acid sequence.

18. An adenovirus comprising the chimeric adenovirus fiber protein of claim 7.

19. The adenovirus of claim 18, wherein the adenovirus is targeted via an adenovirus penton protein, and wherein the adenovirus is not targeted via the chimeric adenovirus fiber protein.

20. A trimer comprising the chimeric adenovirus fiber protein of claim 7.

21. An isolated or purified nucleic acid that encodes the chimeric adenovirus fiber protein of claim 7.

* * * * *

UNITED STATES PATENT AND TRADEMARK OFFICE
CERTIFICATE OF CORRECTION

PATENT NO. : 6,576,456 B2
DATED : June 10, 2003
INVENTOR(S) : Thomas J. Wickham et al.

It is certified that error appears in the above-identified patent and that said Letters Patent is hereby corrected as shown below:

<u>Title page,</u>
Item [*] Notice:, please delete the sentence that reads:
"This patent is subject to a terminal disclaimer."

Signed and Sealed this

Twentieth Day of January, 2004

JON W. DUDAS
*Acting Director of the United States Patent and Trademark Office*